United States Patent [19]

Policastro

[11] Patent Number: 4,739,089

[45] Date of Patent: Apr. 19, 1988

[54] ACYLATION OF POLYSILYLAROMATIC ORGANIC COMPOUNDS AND PRODUCTS OBTAINED THEREFROM

[75] Inventor: Peter P. Policastro, Niskayuna, N.Y.

[73] Assignee: General Electric Company, Schenectady, N.Y.

[21] Appl. No.: 17,417

[22] Filed: Feb. 24, 1987

[51] Int. Cl.$^4$ .............................. C07F 7/08; C07F 7/18
[52] U.S. Cl. ..................................... 556/432; 556/436
[58] Field of Search .............................. 556/432, 436

[56] References Cited

U.S. PATENT DOCUMENTS

| | | | |
|---|---|---|---|
| 3,301,817 | 1/1967 | Wilkus et al. | 556/432 X |
| 3,391,109 | 7/1968 | Wilkus et al. | 556/436 X |
| 4,042,613 | 8/1977 | Takamizawa et al. | 556/436 X |

FOREIGN PATENT DOCUMENTS 2120264  11/1983  United Kingdom ............... 556/436

Primary Examiner—Paul F. Shaver
Attorney, Agent, or Firm—William A. Teoli; James C. Davis, Jr.; James Magee, Jr.

[57] ABSTRACT

A method for making certain silylaryl ketones is provided by acylating a silarylene with an arylacyl halide in the presence of a Friedel-Crafts catalyst. Silicon containing arylketones are also provided.

9 Claims, No Drawings

ACYLATION OF POLYSILYLAROMATIC ORGANIC COMPOUNDS AND PRODUCTS OBTAINED THEREFROM

BACKGROUND OF THE INVENTION

As taught by Wilkus et al., U.S. Pat. Nos. 3,301,817, 3,410,822 and 3,855,241, various aryl nuclei can be monoacylated or diacylated with a silyl acid halide, for example trimethylsilylbutryl chloride, to produce carbinol containing organo silicon materials. In particular instances, diacylation of the aryl nuclei, for example, benzene, is not readily achieved by the Wilkus et al method, unless an indirect procedure is used, such as initially monoacylating the aryl nuclei, reducing the resulting carbinol containing material, followed by the further acylation of the aryl nuclei and the subsequent oxidation of the reduced carbinol radical. Obviously, such a procedure is time consuming and economically unattractive.

The present invention is based on my discovery that a wide variety of silicon containing arylketone monomers can be made by effecting reaction between a polysilylaromatic organic compound of the formula $$R + Si(R^1)_a X_{3-a}]_b, \quad (1)$$

and an arylacyl halide of the formula

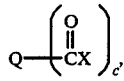
$$Q + \begin{pmatrix} O \\ \parallel \\ CX \end{pmatrix}_c, \quad (2)$$

where R is a $C_{(6-14)}$ polyvalent aromatic organic radical, $R_1$ is selected from $C_{(1-8)}$ monovalent hydrocarbon radicals, substituted $C_{(1-8)}$ monovalent hydrocarbon radicals and a mixture thereof, X is a halogen radical, Q is a member selected from $C_{(6-14)}$ monovalent or polyvalent aryl radicals, and organosilyl radicals included within the formula $$-R-Si(R^1)_a X_{3-a},$$

a is a whole number equal to 0 to 2, b is an integer equal to 2 or 3, and c is an integer equal to 1 or 2.

STATEMENT OF THE INVENTION

There is provided by the present invention, a method for making silicon containing arylketones comprising
(1) effecting reaction between a polysilylaromatic organic compound of formula (1), and an arylacyl halide of formula (2) in the presence of an effective amount of a Friedel-Crafts catalyst, and
(2) recovering silicon containing arylketone from the mixture of (1).

Polyvalentaromatic organic radicals which are included within R of formula (1) are, for example,

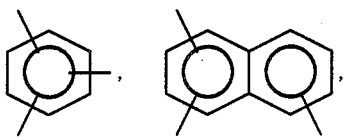

phenylene, naphthylene, anthrylene, phenanthrylene, indylene, etc., and substituted arylene radicals containing halo, alkoxy, alkyl or vinyl groups or mixtures thereof. Polyvalent radicals included within Q of formula (2) are the aforementioned arylene radicals of R. Monovalent hydrocarbon radicals, and such substituted monovalent which are included within $R^1$ of formula 1 are, for example, methyl, ethyl, butyl, cyclohexyl, chloromethyl, and trifluoropropyl. Aryl radicals included within Q of formula (2) are, for example, phenyl, chlorophenyl, methoxyphenyl, methylphenyl, and naphthyl.

Some of the polysilylaromatic organic compounds included within formula (1) are, for example, 1,4-bis(dimethylchlorosilyl)benzene, 1,3-bis(dimethylchlorosilyl) benzene, 1,4-bis(dimethylmethoxysilyl)benzene, 1,4-bis(dimethylethoxysilyl)benzene, 1,3,5-tris(dimethylchlorosilyl) benzene, 1,6-bis(dimethylchlorosilyl)-naphththalene, 2-methoxy-1,4-bis(dimethylchlorosilyl)-benzene. These silarylenes and method for making are well known such as shown by R. L. Merker and M. J. Scott, J.Polym.Sci.A, 2, 15 (1964).

Some of the aryl acylating agents included within formula (2) are, for example, p-dimethylchlorosilylbenzoylchloride, m-dichloromethylsilylbenzoylchloride, naphthylchloride, p-trimethoxysilylbenzoylchloride, o-methoxybenzoylchloride, o-trimethylsiloxybenzoylchloride, m-ethynylbenzoylchloride, p-nitrobenzoylchloride, p-cyanobenzylchloride, m-chlorobenzoylchloride, 3,5-dimethylchlorosilylbenzoylchloride, terephthaloylchloride, isophthaloylchloride, and trimelliticanhydride acid chloride. Some of the silyaryl acylating agents and method for making are shown by J. Rich, copending U.S. Pat. application Ser. No. 765,089, filed Aug. 13, 1985 incorporated herein by reference.

Friedel-Crafts catalysts which can be utilized in the practice of the invention are, for example, aluminum chloride, boron trifluoride, boron trifluoride etherate, tin chloride, zinc chloride, iron chloride, zinc iodide, aluminum bromide, and boron trichloride.

An effective amount of Friedel-Crafts catalysts used in the practice of the present invention is 5 to 50% of catalysts by weight based on the weight of the reaction mixture and preferably 10 to 20%.

The preferred silicon-containing arylketones which can be made by the method of the present invention are silylbenzophenones of the formula

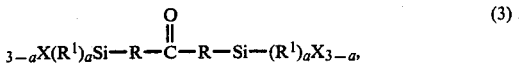
$$_{3-a}X(R^1)_a Si-R-\overset{O}{\underset{\parallel}{C}}-R-Si-(R^1)_a X_{3-a}, \quad (3)$$

where R, $R^1$, X and a are as previously defined. There are included by the silyl arylketones of formula (3) compounds such as
4,4'-bis(dimethylchlorosilyl)benzophenone,
3,4'-bis(dimethylchlorosilyl)benzophenone,
3,3'-bis(dimethylchlorosilyl)benzophenone,
4,4'-bis(dimethoxymethylsilyl)benzophenone, and
3-(3-dimethylchlorosilyl)benzoyl-3'-dimethylchlorosilylbenzophenone.

The silylbenzophenones of the present invention can be hydrolyzed in an aqueous media to produce high temperature fluid, resins, and gums useful in the production of temperature resistant hydrophobic paper coatings and in the practice of the method of the present invention, the polysilylaromatic organic compound referred to hereinafter as the "silphenylene", and the arylacyl halide are heated in the presence of a Friedel-Crafts catalysts while the mixture is agitated. There can be used temperatures in the range of from −78° C. to 200° C., and preferably between 0° C. and 200° C. Depending upon whether monoacylation or diacyation is desired, the molar proportion of the silarylene to the arylacyl halide can vary. For example, in making bisacylarylketone, there can be used equal molar amounts of the silarylene and the arylacyl halide. In other situations there can be used about 2 moles of the silarylene, per mole of the arylacyl halide.

Reaction is generally conducted under neat conditions, and silylalkyl halide can be readily distilled from the mixture. Recovery of the desired silicon containing arylketone can be achieved by allowing the reaction mixture to cool to room temperature, treating the residue with an organic solvent, such as acetone, and refluxing in a hydrocarbon, such as octane. Filtration of the resulting mixture and recrystallization of the product can be used.

The silicon containing arylketones of the present invention can be used as coupling agents, and modifying agents in the production of a variety of organosiloxanes useful as coatings, adhesives, molding compounds and composites.

The following example is given by way of illustration and not by way of limitation. All parts are by weight.

EXAMPLE 1

There was added portion wise over a period of thirty minutes, 9.7 grams (0.073 mold) of aluminum chloride to a homogeneous melt under nitrogen at 100° C. of 17.5 grams (0.066 mole) of 1,4-bis(4-chlorodimethylsilyl)-benzene and 16 grams (0.066 mole) of 4-chlorodimethylsilybenzoylchloride. Exothermic reaction occurred and the resulting mixture became dark brown. Dimethyldichlorosilane evolved out of the mixture. After 30 minutes the mixture was allowed to cool to room temperature and 6 ml dry acetone was added drop wise. The mixture was then refluxed in 250 ml of hexane and filtered. There was obtained 14.4 grams of a white crystalline solid having a melting point of 124°–125° C. The product was 4,4'-bis(chlorodimethylsilyl)benzophenone; it was obtained in a 59% yield. The identity of the product was further confirmed by its IR spectrum. The bissilylbenzophenone is hydrolyzed in an aqueous ether media to produce a linear silicone polymeric solid. The silicone is heated in an extruder. It is extruded onto a copper wire to provide a high temperature resistant insulating coating.

Following the same procedure, there was initially obtained a 55% yield of 3,4-bis(chlorodimethylsilyl)-benzophenone in the form of a solid. An insulated conductor is made following the same procedure.

EXAMPLE 2

1.51 grams terephthaloylchloride and 3.93 grams of 1,4-bis(dimethylchlorosilyl)benzene were heated to provide a homogeneous melt at 120° C. under nitrogen. There was added, all at once, 2.40 grams anhydrous aluminum chloride. The reaction solidified within several minutes to provide a yellow product which was soluble in chloroform. HNMR analysis of the reaction product indicated nearly quantitative conversion of starting materials to provide 4(4-dimethylchlorosilyl)-benzoyl-4-dimethylchlorosilylbenzophenone.

The above silylbenzophenone is hydrolyzed in an aqueous media as described in Example 1 to produce a high temperature resistant extrudable wire coating composition.

While the above examples are directed to only a few of the very many variables which can be utilized in the practice of the present invention, it should be understood that the present invention is directed to a method utilizing a broader variety of silarylenes of formula 1 and arylacyl halides of formula 2 in the presence of a broader variety of Friedel-Crafts catalysts.

What is claimed and sought to be protected by Letters Patent of the United States is as follows:

1. A method for making silicon containing aryl ketones comprising,
   (1) effecting reaction between a polysilylaromatic organic compound of the formula $$R\text{-}[Si(R^1)_aX_{3-a}]_b,$$

and an arylacyl halide of the formula

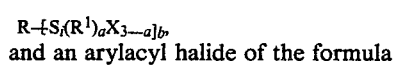

in the presence of an effective amount of Friedel-Crafts catalysts,
   (2) recovering silicon containing arylketone from the mixture of (1), where R is a $C_{(6-14)}$ polyvalent aromatic organic radical, $R^1$ is selected from $C_{(1-8)}$ monovalent hydrocarbon radicals substituted $C_{(1-8)}$ monovalent hydrocarbon radicals and a mixture thereof, X is a halogen radical, Q is a member selected from $C_{(6-14)}$ monovalent or polyvalent aryl radicals, and organosilyl radicals included within the formula $$-R-Si(R^1)_aX_{3-a},$$

a is a whole number equal to 0 to 2 inclusive, b is an integer equal to 2 or 3, and c is an integer equal to 1 or 2.

2. A method in accordance with claim 1, where the acylating agent is

where R is a $C_{(6-14)}$ polyvalent aromatic organic radical, $R^1$ is selected from $C_{(1-8)}$ monovalent hydrocarbon radical, X is a halogen radical, and a is a whole number equal to 0 to 2 inclusive.

3. A method in accordance with claim 1, where the acylating agent is

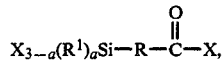

where R is a $C_{(6-14)}$ polyvalent aromatic organic radical, and X is a halogen radical.

4. A method in accordance with claim 1, where the acylating agent is

where Q is a $C_{(6-14)}$ monovalent aryl radical, and X is a halogen radical.

5. Silaryl ketones of the formula

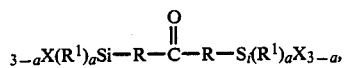

where R is a C$_{(6-14)}$ polyvalent aromatic organic radical, R$^1$ is selected from C$_{(1-8)}$ monovalent hydrocarbon radical, X is a halogen radical, and a is a whole number equal to 0 to 2 inclusive.

6. 4,4'-bis(chlorodimethylsilyl) benzophenone.
7. 3,3'-bis(chlorodimethylsilyl) benzophenone.
8. 3,4'-bis(chlorodimethylsilyl) benzophenone.
9. 4(4-dimethylchlorosilyl)benzoyl-4-dimethylchlorosilyl benzophenone.

* * * * *